United States Patent [19]

Chitwood

[11] Patent Number: 5,052,378

[45] Date of Patent: Oct. 1, 1991

[54] PORTABLE TRACTION APPARATUS

[75] Inventor: Ralph M. Chitwood, Kalispell, Mont.

[73] Assignee: Glacier Cross, Inc., Whitefish, Mont.

[21] Appl. No.: 431,603

[22] Filed: Nov. 3, 1989

[51] Int. Cl.[5] .......................... A61F 5/00; A61F 5/04; A61H 1/02

[52] U.S. Cl. .......................................... 128/71; 128/72; 128/75; 128/84 R

[58] Field of Search ........................ 128/70, 71, 72, 75, 128/84 R, 84 C; 5/67; 269/322; 108/115, 125, 126, 129, 145, 146, 65

[56] References Cited

U.S. PATENT DOCUMENTS

| | | | |
|---|---|---|---|
| 1,642,158 | 9/1927 | Kubista | 128/71 |
| 1,735,569 | 11/1929 | Gregory | 128/71 |
| 2,283,549 | 5/1942 | Galloraith | 128/71 |
| 2,774,349 | 12/1956 | Judovich | 128/71 |
| 3,548,816 | 12/1970 | Bond | 128/75 |
| 4,608,969 | 9/1986 | Hamlin | 128/71 |
| 4,664,101 | 5/1987 | Gramberg | 128/84 R |

FOREIGN PATENT DOCUMENTS

| | | | |
|---|---|---|---|
| 1062843 | 4/1954 | France | 128/72 |

*Primary Examiner*—Richard J. Apley
*Assistant Examiner*—Karen G. Horowitz
*Attorney, Agent, or Firm*—Thomas R. Vigil

[57] ABSTRACT

According to the present invention there is provided a portable traction apparatus including a table having a head end and a foot and including a generally rectangular panel adapted to be placed in a horizontal position. A traction exerting mechanism is mounted to the table and includes an extension linkage assembly fixed to the table and including articulated pivotally interconnected links, an elongate upper end member connected at an inner end to the linkage assembly and having an outer end extending outwardly of the head end of the table and or, an elongate lower end member having an inner end connected to the linkage assembly and an outer end extending outwardly of the foot end of the table and, first and second lever arms pivotally connected to and forming part of the linkage assembly, each lever arm having an outer end extending outwardly from one side of the table and having arm engaging means at the outer end of each lever arm. The lever arms are movable from and to a non-traction exerting position near the head end of the table where one or two elongate end members are in a retracted position within the table and a second position toward the foot end of the table where the extension linkage assembly is extended by the movement of the lever arms so as to extend one or two elongate end members to which body engaging means can be attached for applying traction to a user/patient lying on the table.

76 Claims, 7 Drawing Sheets

PORTABLE TRACTION APPARATUS

BACKGROUND OF THE INVENTION

1. Field of the Invention

The present invention relates to a portable traction apparatus which a user/patient utilizes in a horizontal position for applying patient controlled traction to the cervical spinal region, the lumbar spinal region or both simultaneously, intermittently or continuously over a given time period.

2. Description of the related Art Including Information Disclosed Under 37 CFR §§1.97-1.99

A large segment of the human population suffers from back pain. The back pain symptoms are primarily due to compression of the spinal nerve roots which is produced, in the majority of instances, by trauma, subluxation, narrowed degenerated disc, hypertrophic arthritis, or by a combination of one or more of these events.

Mild compression causes an irritation of the nerve roots, resulting in both local pain and pain along the course of the nerve fibers. Often, muscle spasm is experienced which acts to further draw the vertebrae together. More severe compression involves not only sensory nerve fibers, but also the motor nerve fibers and results in increased pain, as well as flabbiness and weakness of the muscles and, further, diminished reflexes.

Individuals experiencing back pain from spinal compression often seek relief by attempting to stretch the spinal column. A simple technique is hanging the body by either the neck or feet to allow the force of gravity to relieve the compression. However, the forces employed cannot be controlled and may result in more severe injury.

Additionally, applying traction to the body in a vertical position, particularly if the body is suspended by the feet, interrupts the normal flow of blood. Obviously, suspension by the head or neck could result in excessive stretching of the spine.

A telescopic suspension assembly adapted for vertical or inclined use in applying traction by gravity to the lumbar region is sold under the trademark GLR TM Maintenance Unit by Camp, International Inc. of Jackson, Mich.

Heretofore, many traction devices, including traction tables, have been proposed for elongating the spine. For example, the Saunders TM Cervical Traction Unit sold by Chattanooga Corporation of Chattanooga, Tenn., utilizes the traction unit which includes a table and a U-shaped collar and headrest which are situated beneath the head for pulling at the base of the occiput to apply cervical traction while the patient lies on the traction table.

A variety of halters and cervical pillows, including a pelvic belt, a thoracic restraint belt and a cervical pillow can be utilized with the Saunders TM Traction Table for applying traction to different parts of the spine including the lumbar and cervical regions. Such halters and belts include hook fasteners, snap fasteners and hook and loop material such as that sold under the trademark VELCRO fasteners.

Another horizontal table-type traction control unit is sold by Hill Laboratories Company of Melvern, Pa., under the trademark Anatomotor TM. In this device, thoracic and iliac harnesses and an ankle harness are provided for applying intermittent or steady traction (a) to the lumbar area with the ankle harness, (b) to the lumbo-sacral region with the thoracic and iliac harnesses, and (c) to the cervical vertebrae with a head halter or a cervical traction device. The Anatomotor TM also can provide massage through massage rollers at the same time traction is applied. Additionally, heat can be applied as well as vibration. A releasable, lockable, rotatable and extendable arm is provided at one end of the table of the Anatomotor TM and a horizontally positionable and vertically positionable arm assembly is located at the other end of the table and can be locked into a desired position for applying traction at different angles to the patient.

Most previously proposed traction tables, such as the Anatomotor TM, are controlled by the doctor or chiropractor and are limited in the stretching applied, and are not patient controlled while traction is applied.

Some examples of previously proposed traction tables and portable traction apparatus are disclosed in the following U.S. Patents:

| U.S. Pat. No. | Patentee |
|---|---|
| 1,628,369 | McBurney |
| 2,787,262 | Warner |
| 3,353,532 | Ellis |
| 4,102,336 | Wiener et al. |
| 4,608,969 | Hamlin |
| 4,466,427 | Granberg |

The McBurney treatment table disclosed in U.S. Pat. No. 1,628,369 includes swingable tabletop portions whereby a patient can receive traction massages by the tilting and straightening actions of the tiltable tabletop portions. A chin strap and a waist strap are provided by which the upper and lower extremities of the patient may be held to the tilting tabletop portions.

The Warner U.S. Pat. No. 2,787,262 discloses a body traction apparatus with an extensible table whereby traction can be applied to a patient whose ankles are held within a stock on the extensible table by operating a wheel connected to a worm gear that meshes with a worm carried by a shaft for extending the extensible table. A head loop can be provided and anchored to a bracket at the head of the table. The wheel can be operated by the patient.

The Ellis U.S. Pat. No. 3,353,532 discloses a portable traction apparatus which is of the vertical type whereby a person can support himself in a vertical position above the ground by reason of two body engaging members that engage the side of the chest and with the forearms or elbows of the patient resting on armrests.

The Wiener et al. U.S. Pat. No. 4,102,336 discloses an apparatus for traction therapy comprising a tubular framework having handle grips along the side frame members thereof, a raised cross-bar at one end and a strap member at the other end which can be utilized as a pelvic belt.

The Hamlin U.S. Pat. No. 4,608,969 discloses a portable traction table which has a head halter and a chin strap or shoulder restraining straps at one end and leg seating seats and clinch straps for fastening the legs to an extensible part of the table at the other end of the table. A screw shaft and ratchet mechanism are provided for extending the leg seats and straps. A ratchet handle for the ratchet mechanism is located adjacent the table for manipulation by the user.

The Granberg U.S. Pat. No. 4,466,427 discloses a portable traction device including a frame which is placed on a floor and within which a user positions himself on the floor for being subjected to traction. A pelvic belt strap and a thoracic belt are secured about the patient. In a commercial embodiment of the Granberg traction device, a Goodley halter or a chin strap can be utilized to apply cervical traction and a stool can be provided for raising and supporting flexed legs of the user of the device.

An hydraulic mechanism for applying tension to a tensioner member, e.g. a flexible cable, is located on the frame and activated by the user/patient.

The hydraulic mechanism includes a manually operated hydraulic pump connected to the flexible cable. A dump valve is provided to immediately relieve all pressure on the hydraulic cylinder of the hydraulic pump when the patient desires to terminate the treatment.

Cervical traction can be applied between a neck halter connected to a traction post which extends upwardly a set distance above the table and a counter-traction belt around the waist. The traction post is connected to an extendable piston of the hydraulic mechanism.

For pelvic traction, a waist belt is pulled against the counter-traction belt secured around the waist of the patient.

In the Granberg portable traction device, traction can be applied between the cervical halter and a pelvic strap, can be applied between the cervical halter and the counter-action belt, or between the counter-action belt and the pelvic strap.

Recently it has been found that by simultaneously applying traction to both the neck (cervical region) and the lower back (lumbar region) more specific relief can be obtained for the pain causing localized compression. Also, it is desirable that the user patient be able to control the amount as well as the duration of the traction and to be able to choose the vertebrae region to be placed in traction. Additionally, it is desirable that the user/patient be able to apply intermittent, static or continuous traction. With traction applied in this desirable manner, once the patient feels that the amount of force was adequate to relieve pain, such traction force can be applied intermittently or continuously to achieve the relief from pain desired without the possibility of discomfort or injury.

It is also desirable that such traction applying device be portable and inexpensive.

The various traction applying apparatuses and devices described above achieve some but not all of these desirable features. For example, the Hill Laboratories, Inc. Anatomotor TM can be utilized to simultaneously apply traction to the neck and the lower back. Also, it provides for adjustment of the angle at which traction is applied. However, it is not a portable traction device and does not provide the desired user/patient control.

On the other hand, the Granberg portable traction device disclosed in the Granberg U.S. Pat. No. 4,466,427 provides portability and is user/patient controlled for controlling the amount of traction or tension applied. However, it does not provide a raised table surface, a mechanical linkage assembly for applying traction with a mechanical advantage, or instantaneous patient controlled intermittent application of traction.

As will be described in greater detail hereinafter, the portable traction apparatus of the present invention differs from the previously proposed traction applying apparatus and devices by providing a simple in construction, inexpensive and effective patient controlled traction apparatus which utilizes mechanical linkages and mechanical advantage, which is portable, and which has adjustable parts thereby the angle at which traction is applied to the cervical or lumbar regions of the spine can be accurately controlled to focus the traction on a particular vertebra region and which enables intermittent as well as continuous traction to be applied to the user's/patient's spine in the lumbar region and the cervical region separately or simultaneously.

SUMMARY OF THE INVENTION

According to the present invention there is provided a portable traction apparatus including a table having an upper or head end and a lower or foot end and including a generally rectangular panel adapted to be placed in a horizontal position.

A traction exerting mechanism is mounted to the table and includes an extension linkage assembly positioned in a plane generally parallel to the table, fixed to the table and including articulated pivotally interconnected links, and first and second lever arms pivotally connected to and forming part of the linkage assembly, each lever arm having an outer end extending outwardly from one side of the table and arm engaging means at the outer end of each lever arm.

The lever arms are movable in a plane generally parallel to the table from and to a non-traction exerting position toward the upper or head end of the table and a second position toward the lower or foot end of the table where the extension linkage assembly is extended by the movement of the lever arms so as to pull on body engaging means attached thereto for applying traction to a user/patient lying on the table.

Preferably, traction is applied through a lower elongate member, an upper elongate member, or both, each of which is coupled at one end to the linkage assembly and is adapted to be connected at the other end to the body engaging means.

Also preferably, each elongate end member has an upwardly extending member at the outer end thereof and a vertically adjustable strut associated with the generally upwardly extending member.

The body engaging means for engaging one or more parts of the body includes traction applying means adapted to be connected to one of the vertically adjustable struts.

The vertical adjustment of the vertically adjustable struts enable the user/patient to apply traction to different regions of the vertebrae of the spine of a user/patient lying on the table.

The lever arms with arm engaging means allow the user/patient to control the amount of traction force applied by the user/patient's forearm or elbow against the arm engaging means intermittently or continuously.

Also, preferably latching means are provided for latching the traction exerting mechanism in a desired position for the application of continuous traction simultaneously or separately to the cervical and lumbar spinal regions of the user/patient's spine.

Figure 2:
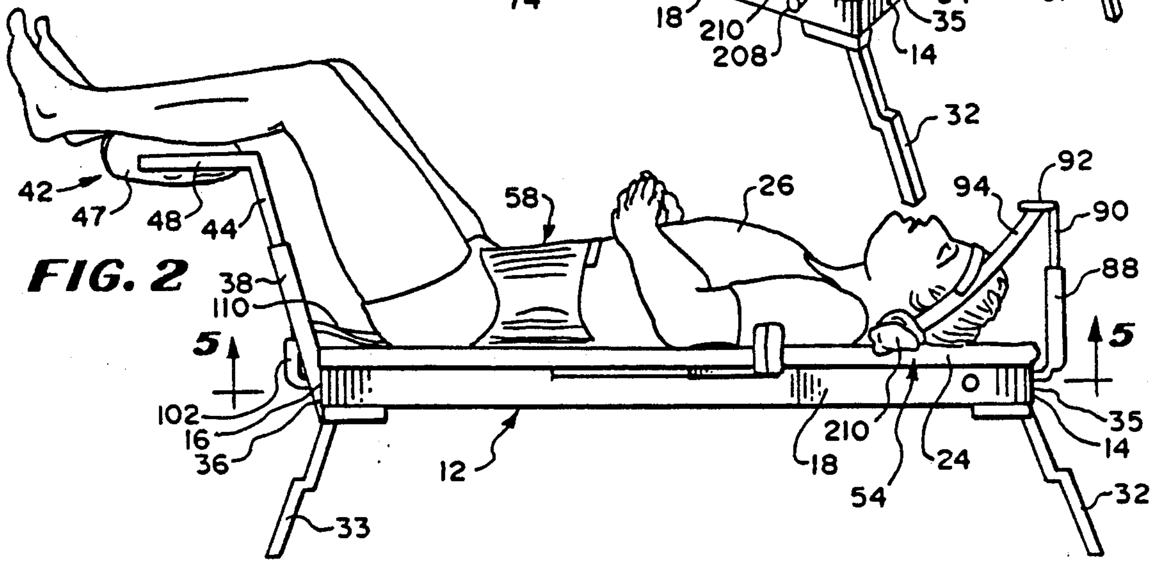
FIG. 2 is a side elevational view of the traction apparatus with a patient resting thereon as shown in FIG. 1 and shown with the traction apparatus in an at rest position.
Figure 3:
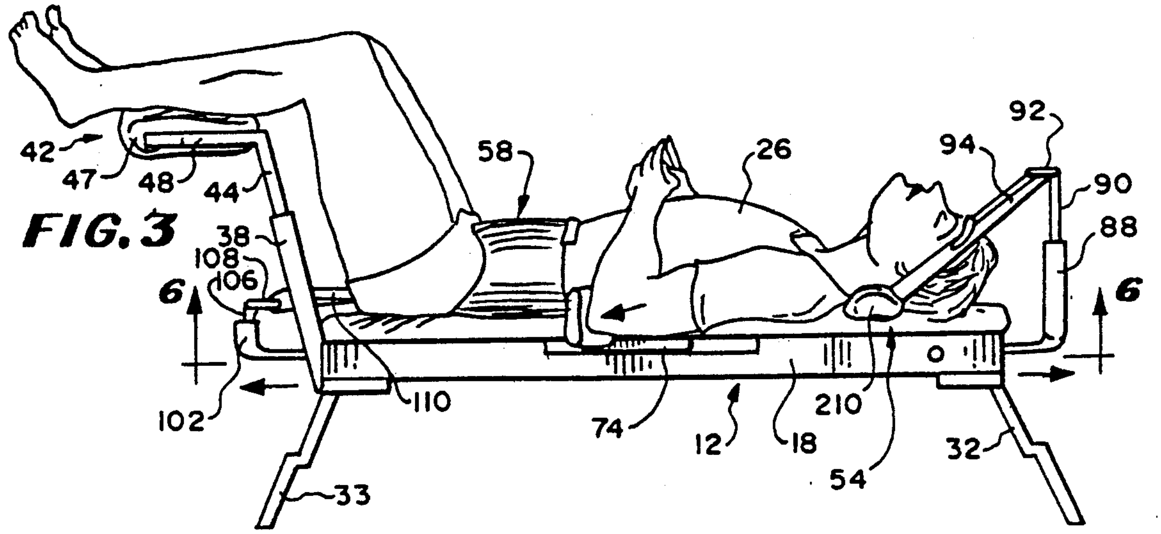

FIG. 3 is a side elevational view, similar to FIG. 2, of the traction apparatus but showing an arm pad which is connected to a lever arm of the apparatus moved to a traction establishing position by the elbow of the patient.

Figure 4:
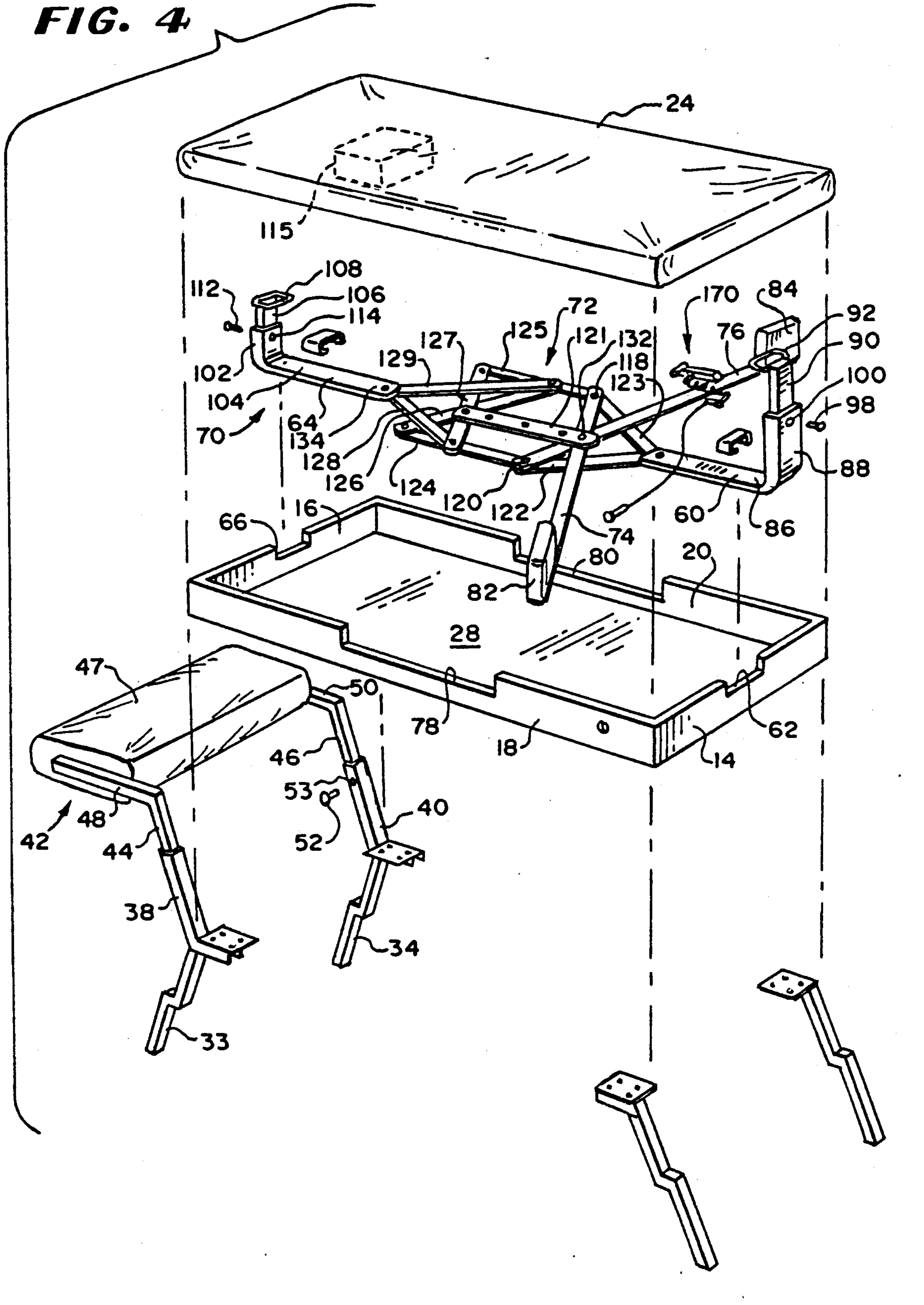

FIG. 4 is an exploded perspective view of the portable traction apparatus of the present invention.

Figure 5:
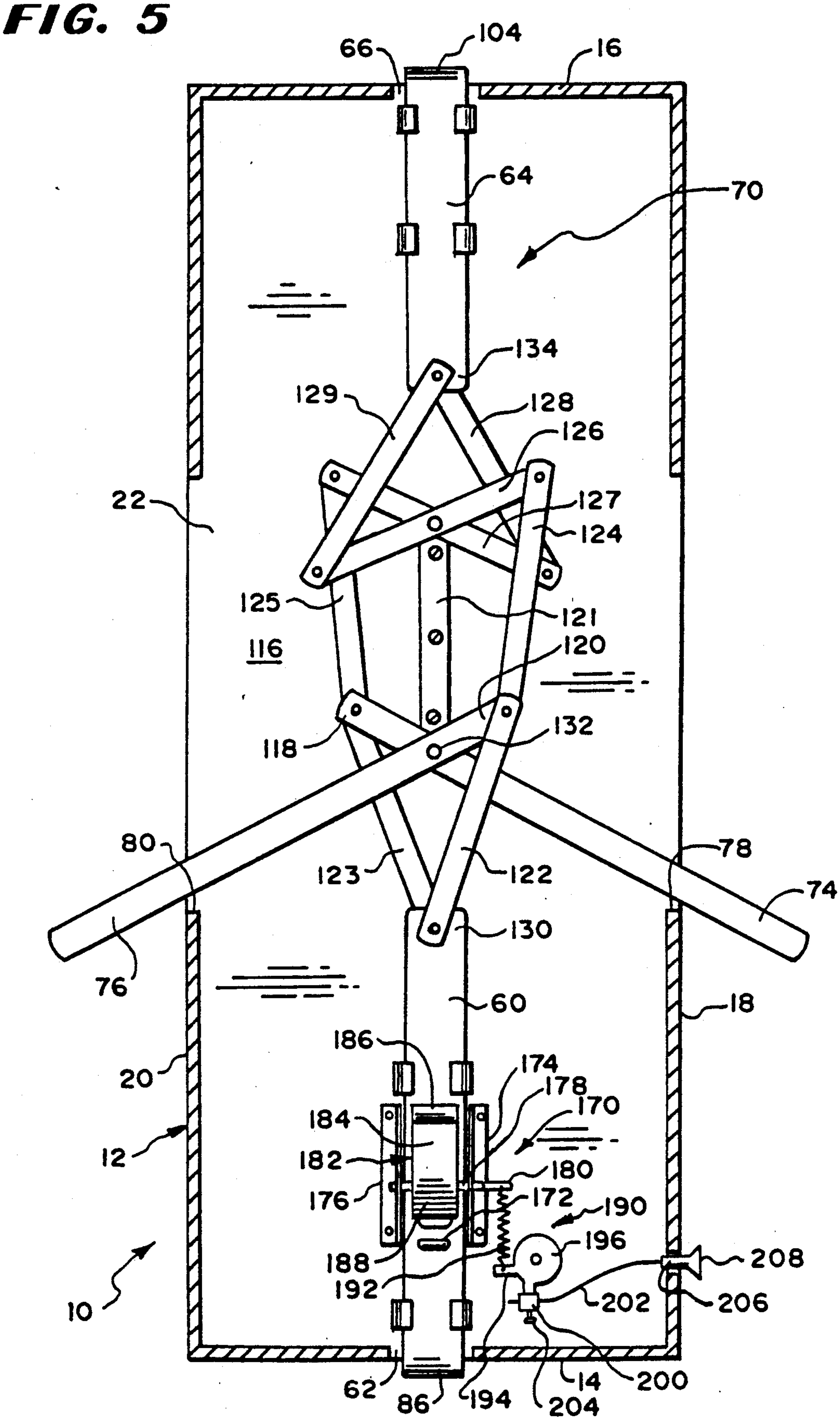

FIG. 5 is a horizontal sectional view taken along line 5—5 of FIG. 2 and shows a bottom plan view of an extension mechanism including an extension linkage assembly operated by two lever arms of the assembly.

Figure 6:
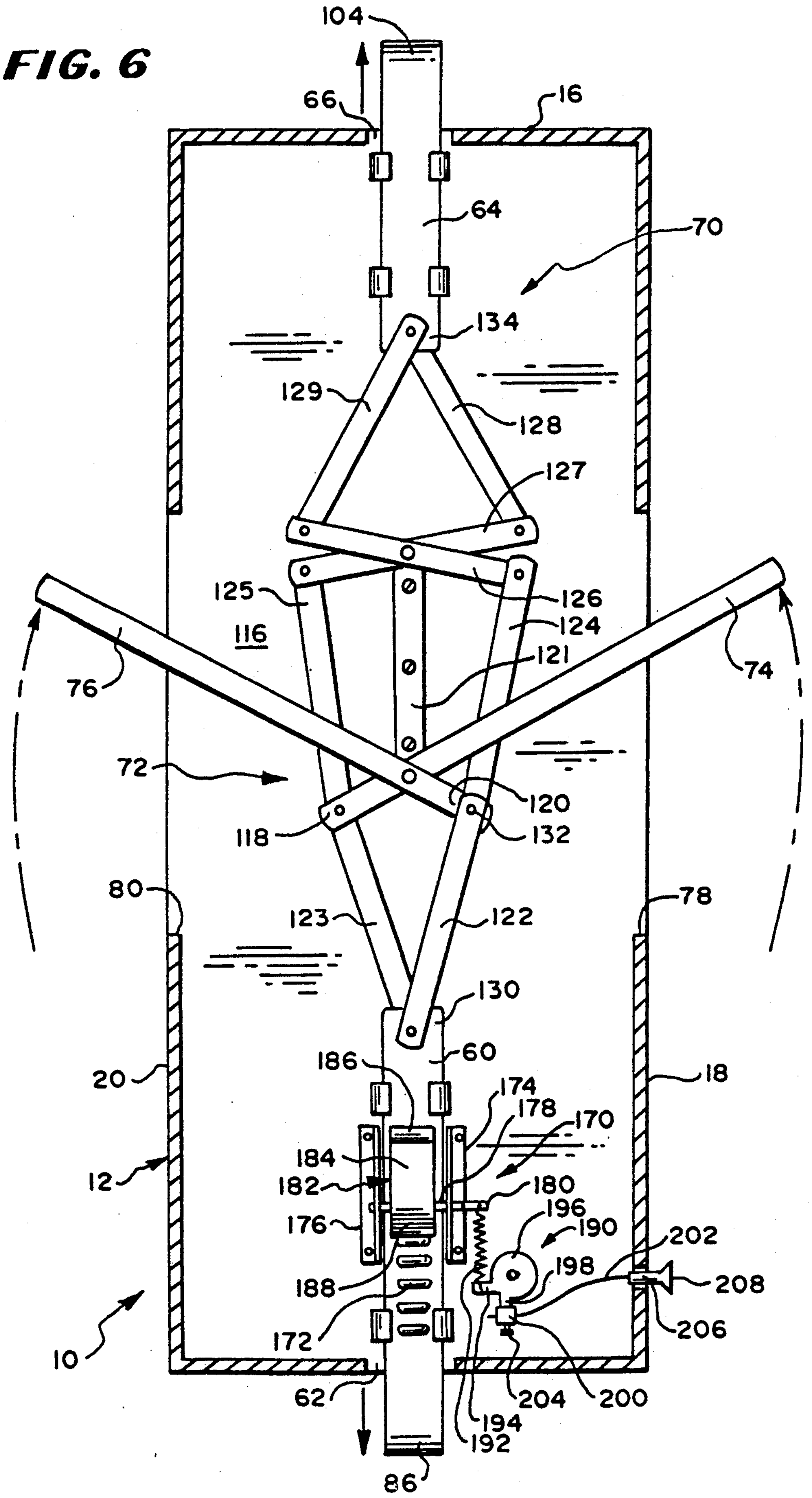

FIG. 6 is a horizontal sectional view taken along line 6—6 of FIG. 3 and shows a bottom plan view of the extension mechanism but shows the two lever arms of the extension linkage assembly moved to a traction exerting position where the extension linkage assembly is extended as shown.

Figure 7:
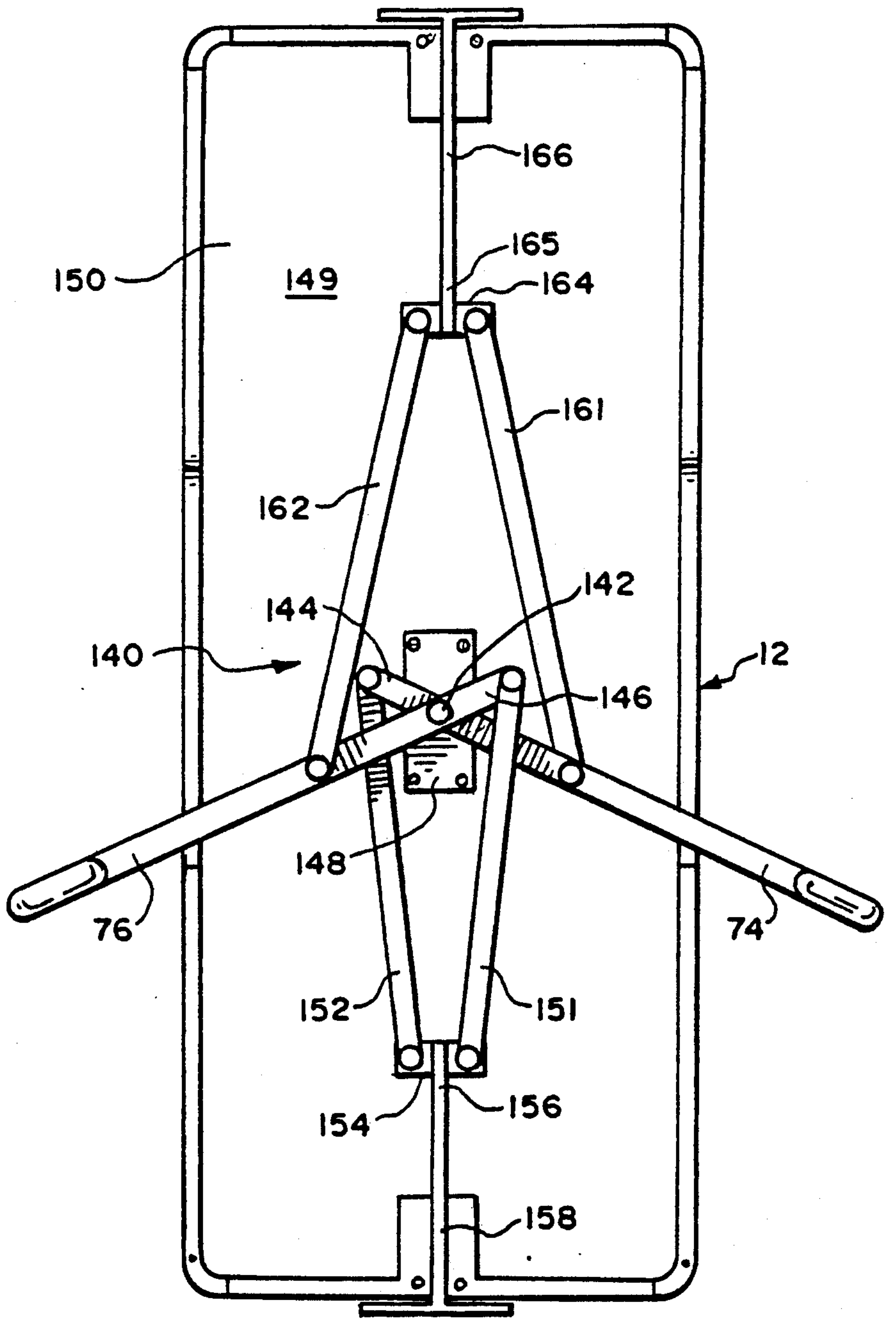

FIG. 7 is a bottom plan view of a modified extension linkage assembly.

Figure 8:
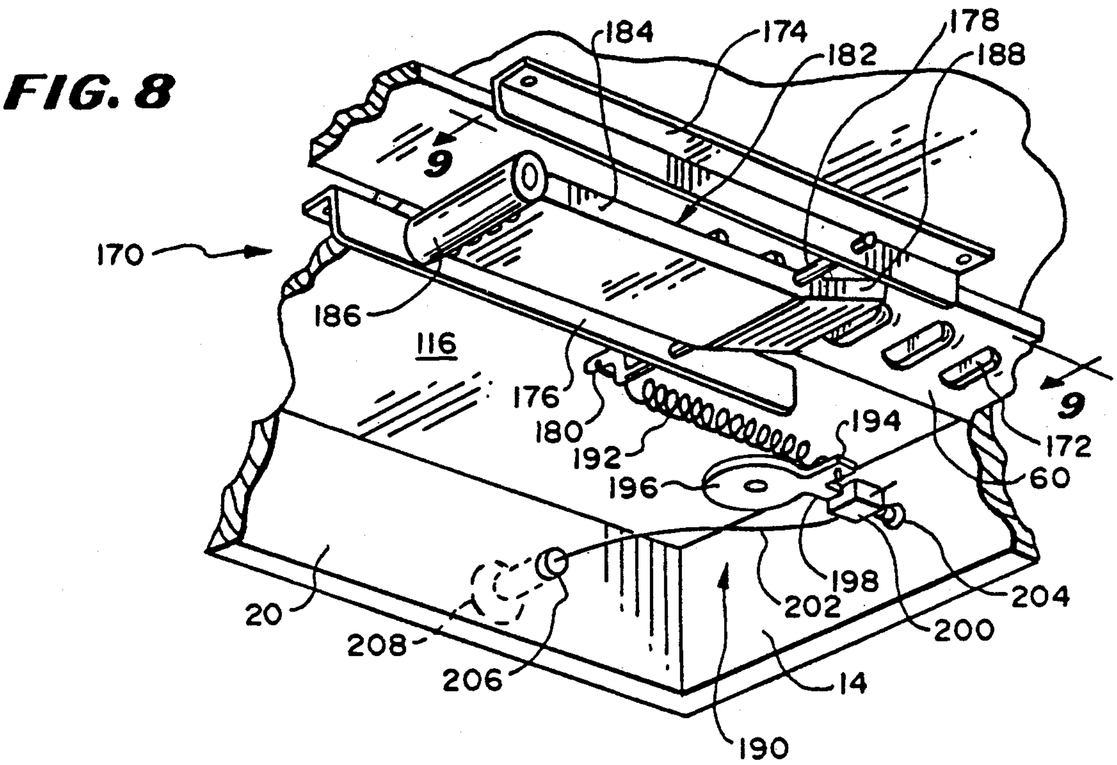

FIG. 8 is a fragmentary perspective view of a latching mechanism mounted within the traction apparatus viewing latching mechanism from beneath the apparatus.

Figure 9A:
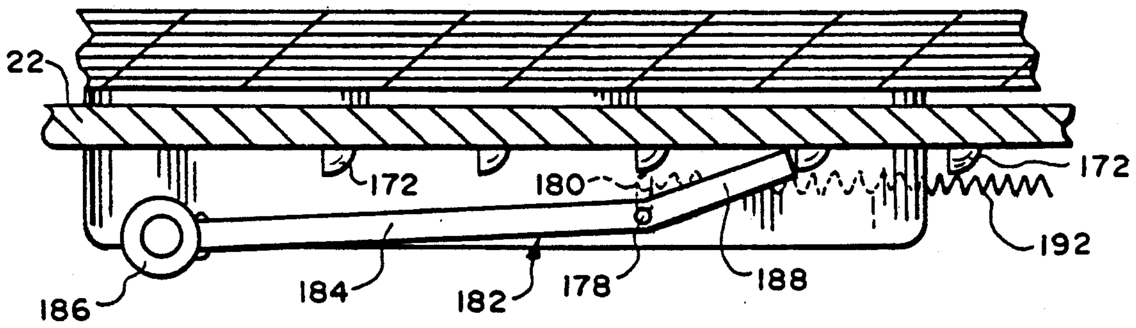

FIG. 9A is a vertical sectional view of the latching mechanism taken along line 9—9 of FIG. 8 and shows the mechanism in a latched position to hold the traction apparatus in a stationary traction exerting position.

Figure 9B:
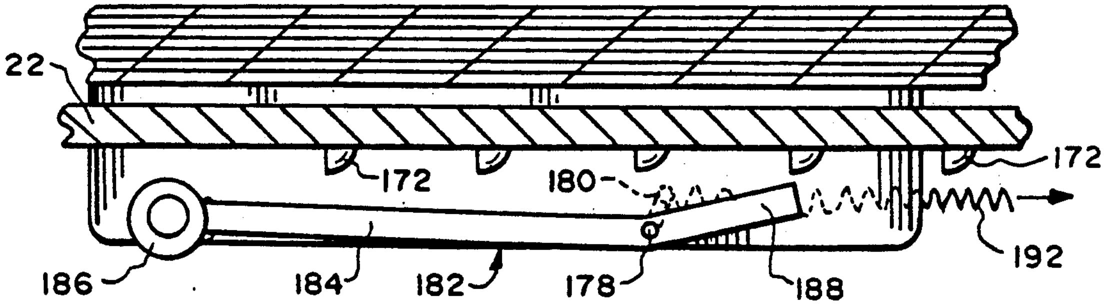

FIG. 9B is a vertical sectional view of the latching mechanism taken along line 9—9 of FIG. 8 and shows the mechanism in an unlatched position.

Figure 10:
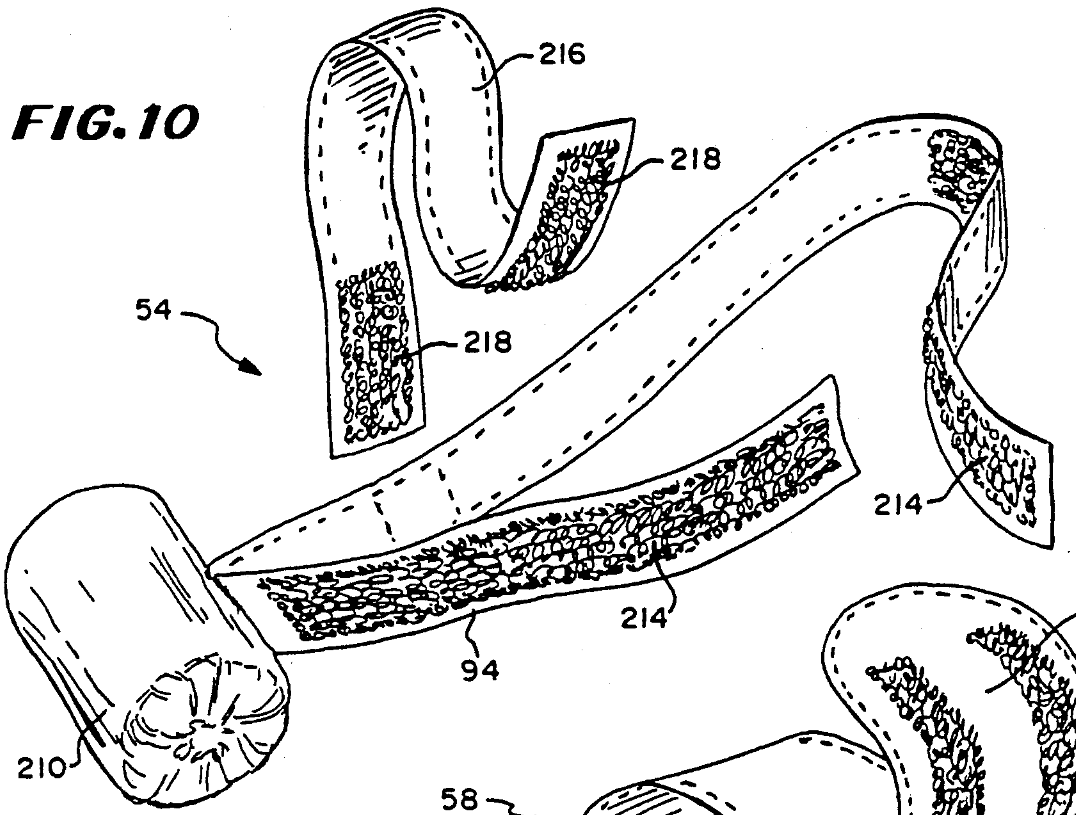

FIG. 10 is a perspective view of a cervical/neck pillow and head strap assembly.

Figure 11:
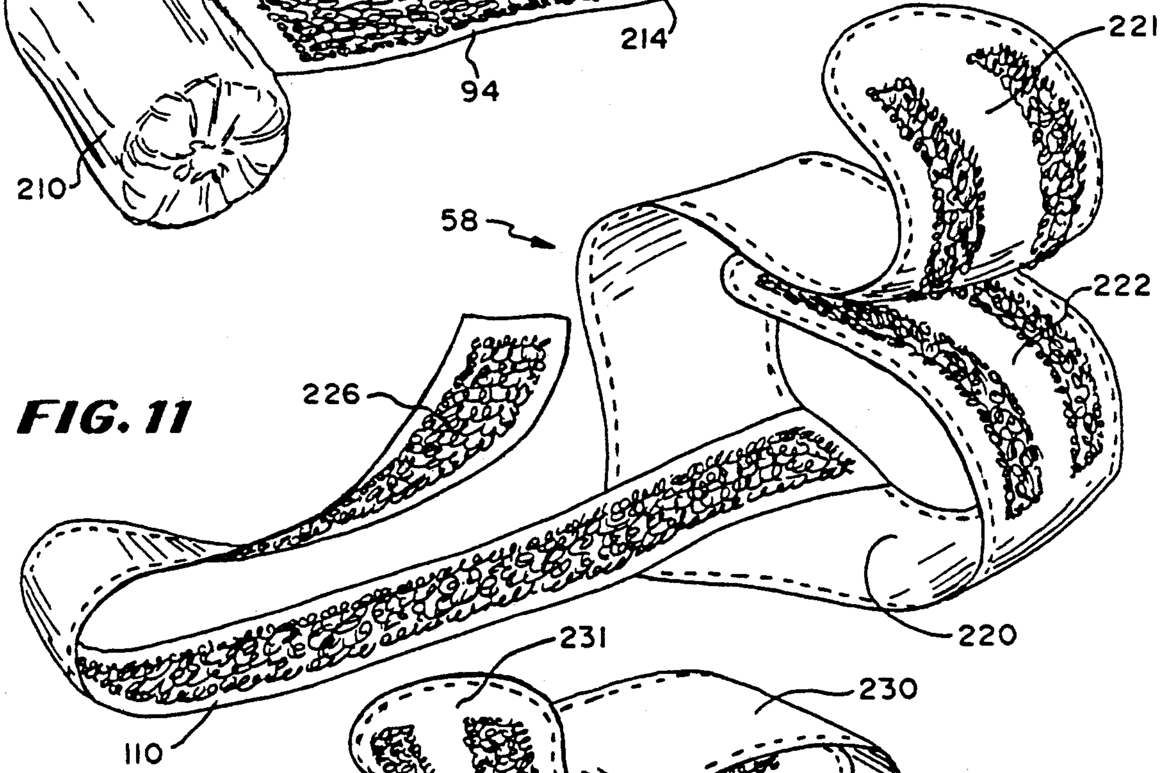

FIG. 11 is a perspective view of a lumbar/hip-pelvic strap assembly.

Figure 12:
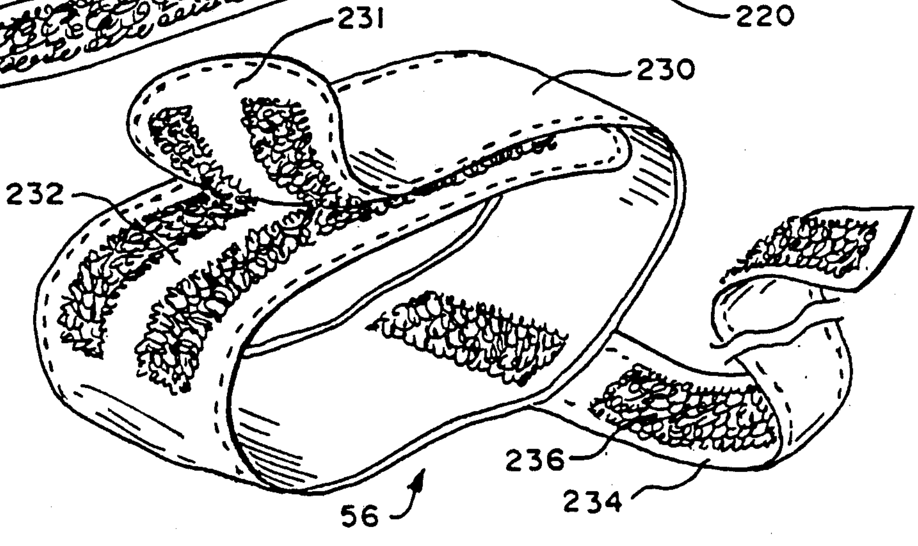

FIG. 12 is a perspective view of a chest strap assembly.

DESCRIPTION OF THE PREFERRED EMBODIMENT

Figure 1:
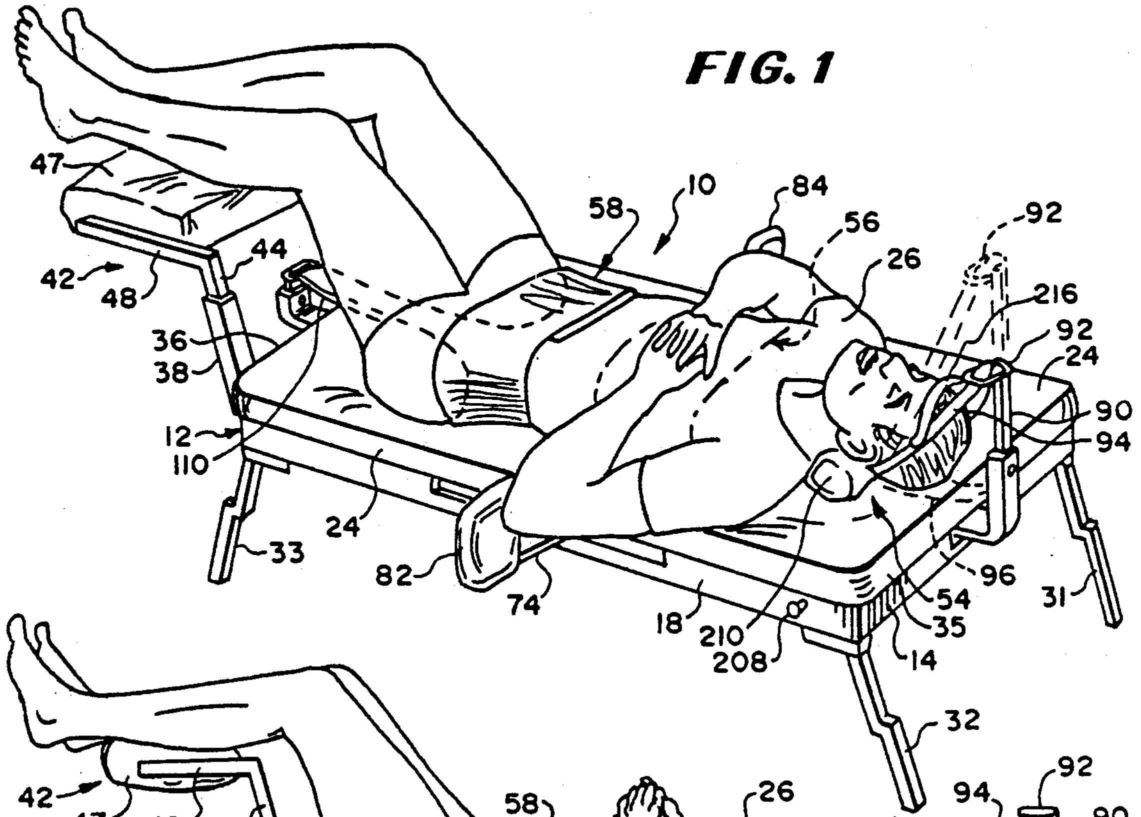
FIG. 1 is a perspective view of a portable traction apparatus constructed in accordance with the teachings of the present invention and shows a user/patient resting thereon.

Referring now to the drawings in greater detail, there is illustrated in FIG. 1 a portable traction apparatus 10 constructed according to the teachings of the present invention. As shown, the apparatus 10 includes a generally rectangular table 12 having opposed upper and lower end walls 14 and 16 (FIG.4), opposed side walls 18 and 20 (FIG.4), a top wall panel 22 (FIG.5) with a generally rectangular mat or pad 24 situated thereon upon which a user or patient 26 will lie in the manner shown in FIGS. 1-3, and a bottom wall panel 28 (FIG.4).

As best shown in FIG.4, the table 12 has four pivotally mounted legs 31-34 at each corner thereof for supporting the table 12 of the apparatus 10 on a flat surface and are foldable beneath the side walls 18, 20 of the table 12 and have offset lower end portion which can form handles when the legs 31-34 are folded under the table 12 in a generally vertical position, much like carrying a suitcase. The table has an upper or head end 35 and a lower or foot end 36.

At the lower or foot end 36 of the table 12, there are provided two tubular members 38 and 40 which are spaced apart and which extend angularly upwardly, respectively, from each corner of the table 12 at the lower or foot end 36. The tubular members 38 and 40 form part of an adjustable leg rest assembly 42 comprising two depending legs 44 and 46 which are telescopingly received in the tubular members 38 and 40. The leg rest assembly 42 further comprises a leg/calf cushion or pad 47 which is mounted to and between two bars 48 and 50 which extend generally horizontally when the leg rest assembly is mounted to the traction apparatus 10 and which are integral, respectively, with one of the depending legs 44 and 46, as shown in FIGS. 1-3.

Each leg 44 and 46 is slidably and adjustably received in one of the tubular members 38, 40, whereby the height of the cushion 47 can be adjusted by moving the legs 44, 46 within the tubular members 38, 40 and then locking them in place with a conventional locking mechanism, such as, for example, a pin 52 (FIG.4) which extends through a throughbore extending through one of the tubular members 38, 40 and then through a selected one of several holes (not shown) in one of the legs 44, 46 received in that tubular member 38, 40.

In FIG. 1, there is illustrated a cervical/neck pillow and strap assembly 54 which will be described in greater detail in connection with the description of FIG. 10, a thorac/chest strap assembly 56, shown in phantom in FIG. 1, which will be described in greater detail in connection with the description of FIG. 11, and a lumbar/hip-pelvic strap assembly 58 which will be described in greater detail in connection with the description of FIG. 11.

As shown in FIGS. 1-6, an elongate upper end extension plate 60 extends out of a slot 62 in the upper end wall !4 and an elongate lower end extension plate 64 extends outwardly from a slot 66 in the lower end wall 16.

The elongate plates 60 and 64 form part of a traction exerting mechanism 70 which also includes an extension linkage assembly 72 mounted within the table 12 between the end plates 60 and 64 as illustrated in FIGS. 4, 5 and 6.

First and second lever arms 74 and 76 are connected within the table 12 to (and form part of) the extension linkage assembly 72 and extend outwardly through slots 78, 80 in respective ones of the side walls 18 and 20. Mounted at each end of each lever arm 74, 76 is a forearm or elbow engaging arm pad 82, 84 by which the user/patient 26 can engage the traction exerting mechanism 70 for extending the extension linkage assembly 72 and thereby the extension plates 60, 64 for exerting traction on the user/patients vertebrae, as will be described in greater detail hereinafter.

The upper end extension plate 60 has at its outer end 86 a generally upwardly extending tubular member 88. Positioned in this tubular member 88 is a telescopic strut or rod 90 having a head end ring or clasp 92 to which a strap 94 of the cervical strap assembly 54 can be attached or to which a strap 234 of the chest strap assembly 56 can be attached.

The telescoping rod or strut 90 can be adjustably locked in place by a suitable locking mechanism such as a pin 98 which is received through a throughbore 100 extending transversely through the tubular member 88 and through a selected one of several holes (not shown) in the telescoping rod or strut 90. In this way, the angle at which the strap 94 or the strap 234 extends from the head end ring or clasp 92 to the head or chest of the user/patient 26 can be controlled or adjusted for focusing the traction applied with the apparatus 10 on selected vertebrae of the spine.

The elongate plate 64 at the foot end 36 of the table 12 also has an upwardly extending tubular member 102 at an outer end 104 thereof. A telescoping rod or strut 106 having a foot end or ring clasp 108 at the upper end thereof is adjustably and telescopically received in said tubular member 102. A strap 110 of the lumbar strap assembly 58 is adapted to be releasably tied or fixed to the foot end ring or clasp 108 and the height of the foot end ring or clasp 108 can be adjusted as desired so that the strap 110 extends at a desired angle from the horizontal to the remainder of the lumbar strap assembly 58 for focusing traction on a desired vertebrae region of the spine when a user/patient 26 engages the pads 82 and 84 and moves the traction exerting mechanism 70 to exert traction on the spine.

For this purpose, an adjustable locking mechanism is provided, such as a pin 112 which is received through a throughbore 114 extending transversely &through the tubular member 102 and through a selective one of several spaced apart holes (not shown) in the telescoping rod or strut 106.

An exploded view of the traction apparatus 10 is shown in FIG. 4. Here it is seen that the apparatus 10 can also include a vibrator mechanism 115, shown in phantom, mounted to the underside 116 of the top wall panel 22 whereby vibration therapy can be supplied to the user/patient 26 in addition to the application of traction to the lumbar region of the spine. The vibrator 115 is shown mounted toward the lower end 36 of the table 12 but preferably may be mounted in the center of the table 12 in the area of a middle link 121 of the linkage assembly 72.

As shown in FIG. 4, the traction exertion mechanism 70 and the extension linkage assembly 72 thereof can be supported in part by the bottom wall panel 28 and is preferably mounted to the underside 116 of the top wall panel 22. The upper/head end elongate plate 60 and the lower/foot end elongate plate 64 which are pivotally connected at their respective inner ends 130 and 134 to the extension linkage assembly 72 which includes a plurality of articulated, pivotally connected links 121-129 which provide a mechanical advantage when the two outwardly extending lever arms 74, 76 of the extension linkage assembly 72 are moved by the user/-patient 26.

As shown in FIGS. 4, 5 and 6, the linkage assembly 72 includes a middle link 121 which is fixed to the underside 116 of the top wall 22 (or to the bottom wall panel 28 if desired) by one, two or three bolts with the elongate axis thereof in axial alignment with the elongate axes of the elongate upper/head end plate 60 and the elongate lower/foot end plate 64.

Each of the lever arms 74 and 76 is pivotally connected at 132 to the middle link 121 a short distance from the respective inner end 118, 120 of each lever arm 74, 76 and at a point on the middle link 121 which is closer to the upper/head end plate 60. First and second upper side links 122, 123 are pivotally connected to an inner end 130 of the upper/head end elongate plate 60. The inner end of each of these side upper links 122, 123 is pivoted to the end 118, 120,respectively, of one of said lever arms 74, 76 and to one end of a connecting link 124 or 125.

First and second cross-links 126, 127 are pivotally connected intermediate the ends thereof to the middle link 121, at a point on the middle link 121 which is closer to the lower/foot end plate 64. One end of each of the cross-links 126, 127 is connected to the other end of one of the connecting links 124, 125.

First and second side lower links 128 and 129 are each pivotally connected at one end to an inner end 134 of said lower/foot end plate 64 and at the other end thereof to the other end of one of said cross-links 126, 127.

From an inspection of FIGS. 4, 5 and 6, it will be apparent that when the lever arms 74 and 76 are moved by a user/patient 26, the lever arms 74 and 76 will pivot about their pivot connection 132 to the middle link 121 which will cause the first and second side upper links 122, 123 to move toward the upper end 35 of the table 12 to move the upper end plate 60 outwardly from the table 12 a distance of up to 5 inches.

At the same time, the inner ends 118, 120 of the lever arms 74 and 76 will pull the connecting links 124, 125 toward the upper end 35 of the table 12 causing the cross-links 126, 127 pivotally connected to the middle link 121 to move about that pivot connection so as to force the lower side links 128, 129 toward the lower end 36 of the table 12, thereby to push the elongate lower end plate 64 out of the table 12 of up to 5 inches. This extended position of the extension linkage assembly 72 is shown in FIG. 6 where the total extension by both end plates 60, 64 is 8.5 inches.

In FIG. 7 is shown another linkage assembly 140 with the lever arms 74, 76 in an at rest position. Here the lever arms 74 and 76 are pivotally connected at a point 142 spaced inwardly from their inner ends 144, 146 to a pivot plate 148 fixed to the underside 149 of a top wall panel 150 of the table 12.

First and second upper end links 151 and 152 are each pivoted at one end to the inner end 144, 146 of one of the lever arms 74, 76 and at the other end to a cross bar 154 fixed to an inner end 156 of an elongate upper end plate 158.

Then, first and second lower end links 161 and 162 are pivoted at one end to one of the lever arms 74, 76 at a point between the outer end of each lever arm 144, 146 and the pivot connection 142 of each lever arm 144, 146 to the pivot plate 148. The other end of each of the lower end links 161, 162 are pivotally connected to a cross bar 164 mounted at the inner end of an elongate lower end plate 166.

It will be apparent that movement of the outer ends of the lever arms 74, 76 upwardly in the plane of FIG. 7 will cause the upper end links 151, 152 to move toward the upper end of the table 12 and the lower end links 161, 162 to move toward the lower end of the table 12.

The extension linkage assembly 72 shown in FIGS. 4, 5, and 6 is preferred, since it is believed that a greater mechanical advantage is obtained with the links 121–129 and their pivot interconnections in the extension linkage assembly 72.

Referring now to FIGS. 4, 8, 9A and 9B, it will be observed that a latching mechanism 170 is provided for latching the upper end plate 60 in a desired position of traction.

As best shown in FIG. 8, the latching mechanism 170 includes a plurality of spaced apart detents 172 on one side of the elongate upper end plate 60. Positioned on either side of the plate 60 and fixed to the under side 116 of the top wall panel 22 are two elongate frame members 174 and 176 between which a pivot shaft 178 of a crank arm 180 is pivotally mounted.

The pivot shaft 178 extends between the frame members 174 and 176 through an elongate planar bar 182 and is rigidly fixed to the bar 182. A long leg portion 184 of the elongate bar 182 extends toward the lower end of the table 12 and has a weight 186 at the outer end thereof. A short, angled or inclined leg portion 188 of the bar 182 extends slightly upwardly and toward the upper end 35 of the table 12. In the absence of any force applied to the crank arm 180, the weighted long leg portion 184 of the bar 182 will move downwardly under the force of gravity causing the outer end of the short leg portion 188 to engage the elongate upper end plate 60 or a detent 172 extending therefrom.

A control linkage assembly 190 provided for pulling the crank arm 180 to rotate the pivot shaft 178 to move the short leg portion 188 out of engagement with the detents 172 when it is actuated. The control linkage assembly 190 shown herein includes a spring 192 coupled between the crank arm 180 and a lug 194 extending outwardly from a disc 196 pivotally mounted to the underside 116 of the top wall panel 22.

Another lug 198 extending outwardly from the disc 196 has a block 200 for receiving and clamping a control wire 202. A thumb screw 204 is provided for releasably clamping the control wire 202 within the block 200. The other end of the control wire 202 is connected to the inner end of a plunger 206 which is slidably mounted to either side wall 18 or 20 of the table 12.

A control knob 208 (FIG. 1) at the outer end of the plunger 206 can be pulled (much like a choke knob for a gasoline engine) for disengaging the outer end of the short leg portion 188 of the bar 182 from one of the detents 172.

It will be understood, of course, that any suitable latching mechanism can be employed for latching the traction exerting mechanism 70 in any particular extended position thereof.

The cervical strap assembly 54 is shown in FIG. 10 and includes a generally cylindrical neck pillow 210 to which is attached the elongate strap 94 which is adapted to be received through the head end clasp 92 and then fixed back upon itself with some tension by means of opposed gripping means 214, such as hook and loop material such as that sold under the trademark VELCRO on one of both sides of the strap 94. An over-the-forehead strap 216 is also provided for being received over the head of the user/patient 26, as shown in FIGS. 1–3, and fixed to the strap 94 by attachment means 218, such as hook and loop material such as that sold under the trademark VELCRO.

The lumbar strap assembly 58 is shown in FIG. 11 and includes a halter 220 which is adapted to be received under the waist and then releasably and snugly fixed over the stomach by adjustable attachment means, such as hook and loop material such as that sold under the trademark VELCRO on opposed surfaces 221, 222 of the halter 220. This strap assembly 58 also includes the crotch strap 110 which is adapted to extend to and through the foot end clasp 108 snugly tightened and then fixed upon itself by attachment means 226, such as Velcro TM on the crotch strap 110.

In FIG. 12, there is shown the chest strap assembly 56 which includes a halter 230 which is adapted to be received under the patient's back and releasably fixed around the user/patient 26. For this purpose, attachment means, such as hook and loop material such as that sold under the trademark VELCRO, is provided on opposed surfaces 231, 232 of the halter 230 whereby the halter 230 can be releasably and snugly fixed about the chest of the user/patient 26. The chest strap assembly 56 is substantially identical to the lumbar strap assembly 58, the only difference being that the length of the attachment strap 234 is greater than the length of the crotch strap 110.

Extending from the halter 230 is an elongate attachment strap 234 which is adapted to be inserted through the head end clasp 92, pulled snugly, and then fastened back upon itself by attachment means 236 on one side of the strap 234, such as hook and loop material such as that sold under the trademark VELCRO.

The tubular members 88 and 102 at the outer ends, respectively, of the elongate end plates 60 and 64 are shown as having different lengths which can range from 0 inches to 18 inches. In one preferred embodiment, the tubular members 88 and 102 were both long enough to accommodate a telescoping rod or strut 90, 106 with an adjustable telescope of approximately 12 inches. This provides an angular displacement of the strap 94 from approximately 0° to the horizontal to approximately 45° to the horizontal, and preferably to at least 30°.

The extent to which the telescoping rods or struts 90 or 106 are raised and latched in placed depends upon the vertebrae area to be treated with traction. In this respect, the higher the height of the clasp 92, the higher up the cervical traction will be applied. Thus, if one wanted to treat the uppermost cervical vertebra C1 or the disc between the first and second cervical vertebrae C1 and C2, one would raise the telescoping rod 90 to its highest position and connect the strap 94 of the cervical strap assembly 54 to the clasp 90, fix the head strap 216 around the head and apply traction with the elbows, as shown in FIG. 3.

Typically, traction is applied with the cervical strap assembly 54 without connecting the lumbar strap assembly 58. However, when the user/patient 26 is of small weight, the lumbar strap assembly 58 is loosely fixed to the foot end clasp 108 to keep the user/patient 26 from sliding on the mat 24 when traction is applied with the elbows against the arm pads 82, 84 at the outer ends, respectively, of the lever arms 74, 76.

Intermittent traction can be applied to the cervical vertebrae by pressing the elbows against the arm pads 82, 84 and then releasing the pressure intermittently.

If continuous cervical traction is desired, the user/patient 26 can not only fix (or have fixed by a therapist) the strap 94 to the clasp 92 and the strap 110 of the lumbar strap assembly 58 to the clasp 108 and then, the patient or the therapist, after pushing in the plunger 206 to allow the latch bar 182 to latch the traction apparatus 10 in a desired position of traction, can move the lever arms 74, 76 to a desired position of relief or traction treatment, with the lever arms 74, 76 automatically locking in place.

In treating the lumbar vertebrae, one would fasten the lumbar strap assembly 58 about the waist, as shown in FIGS. 1–3, and fix (or have fixed by a therapist) the strap 110 to the foot end clasp 108. Then, the user/patient 26 would apply pressure on the arm pads 82, 84 to move the lever arms 74, 76 to apply pressure to the lumbar vertebrae. Again, to apply traction to a specific lumbar region, one would adjust the height of the clasp 108 and telescoping rod 106 to obtain a desired upward angle of pull or traction, i.e. between 0° and 45° to the horizontal and preferably to at least 30° to achieve traction on the desired lumbar region.

If it is desired to apply continuous traction to the lumbar region for an extended period of time, then one would connect the chest strap assembly 56 around the chest and connect the strap 234 snugly to the head end clasp 92, such that the strap 234 is pulling generally horizontally. This is required so that the user/patient 26 does not have to maintain continuous pressure on the arm pads 82, 84 and to maintain his waist and chest in the same position, i.e. to prevent him from sliding downwardly on the mat 24 when the plunger 206 is placed in a latching position. Traction is primarily utilized to trigger physiological responses in the body as follows:

1. Static Traction:
a. Relieves muscle spasms via causing the muscle to assume a position of physiologic rest.
b. Immobilizes or splints parts.
2. Intermittent Traction:
a. Dissipates edema (fluid in extracellular tissues) and congestion.
b. Triggers proprioceptive reflexes.
3. Static or Intermittent Traction:
a. Separation of spinal segments and/or extraspinal joint surfaces.
b. Promotes distraction and gliding of facet joints.
c. Stretches fibrotic tissues and breaks adhesions.

CONTRAINDICATIONS FOR TRACTION

Static/Continuous Traction:
- Cachexia, Advanced
- Cancer
- Advanced Cardiovascular Disease
- Healing Fractures
- Hemorrhagic States
- Hiatal Hernia (thoraco-lumbar traction)
- Uncontrolled Hypertension
- Acute Inflammation
- Joint Instability
- Local Osteomyelitis (infection)
- Osteomalacia
- Osteoporosis
- Pregnancy—Later stages
- Spinal Cord Compression or Pathology Intermittent Traction:
In addition to all above:
- Acute Intervertebral Disc Syndrome
- Severe Muscle Spasm
- Acute Musculoskeletal Inflammation
- Myofascitis
- Bursitis
- Acute Inflammatory Arthritis
- Rheumatoid Arthritis
- Tendinitis Other Considerations:
Should a patient under traction complain of dizziness, nausea, undue discomfort, or sensory changes, e.g. numbness, the traction should be discontinued immediately.

With these responses in mind, the following is a list of conditions for which traction can be used in treatment.

Static or Continuous Traction:
- Articular Jamming
- Compression Fractures
- Early Stage Disc Problems
- Joint Hypomobility
- Lordosis
- Osteoarthritis
- Scoliosis
- Spondylolisthesis
- Stimulation of Mechandreceptors
- Uncomplicated Whiplash Syndrome
- Brachial Neuritis
- Degenerative Disc Disease
- Interverbral Foramin Narrowing
- Kyphosis
- Occipital Neuralgia
- Perivertebral Adhesions and Contractures
- Spasticity
- Sprains
- Subacute Torticollis Intermittent Traction:
- Intervertebral Disc Hydration Deficiency
- Perivertebral Congestion
- Perivertebral Hypotonicity
- Vascular and Lymphatic Stasis As is evidenced by the above list, traction has may uses in the care of numerous ailments.

The portable traction apparatus 10, providing both lumbar and cervical traction, along with static or intermittent traction, offers a unique combination of therapy options to a practitioner.

The traction apparatus 10 is relatively light weight, easily applied after initial instruction, and it is estimated that it will be relatively inexpensive to mass produce and sell.

If desired, an accurate dynamometer can be used with the apparats 10 to ensure that specific pounds of traction are applied. Cervical traction should not exceed 30 pounds.

Also, it is to be understood that the control knob 208 can be located at any desired position, such as adjacent the lumbar region when the patient is lying on the mat 24 to facilitate locking of the apparatus 10 in a desired position.

With the addition of the vibration mechanism 115 to the apparatus 10, an additional benefit of patient relaxation and even patient compliance with a recommended treatment regime is provided.

The portable traction apparatus can be utilized in a clinical setting, can be used by many physicians, physical therapists and sports related practitioners who need portable equipment to use in limited space, for house calls or team activities and by users/patients in their homes or offices. It is ideal for use in the home. Also, it is believed that more health professionals will use traction when it is available with the relatively inexpensive portable traction apparatus 10 of the present invention.

In the use of the portable traction apparatus 10, the degree of traction is determined by the positioning of the strap equipment. Also, it may be necessary to reposition the lumbar halter 220 after tractioning the first time. One should be sure there is no slack in the lumbar crotch strap 110.

Attach the cervical strap 94 first. The base of the strap 94 on the pillow 210 should be placed towards the neck, come up over the ears and fastened to the ring clasp 92.

Then the lumbar halter 220 is angled up and over the back of the hips and down and over the front of the hips ending in a criss cross position. Tightness of this halter is important in achieving full benefits.

When tractioning the cervical vertebrae only, one attaches the lumbar strap loosely. When tractioning the lumbar only, place the head over the pillow, and do not use the head strap equipment. The legs should be elevated as shown in FIGS. 1-3, preferably with the thighs angled downwardly at an angle of approximately 45° to the horizontal. For maximum lumbar traction, once the lever arms 74, 76 are extended, push the elbows down on the arm pads 82, 84 and pull body upwards.

Push in on the control knob 208. Push down on the arm pads 82, 84, and relax. Push down again and relax until desired traction is felt. One may continue to extend the lever arms downward and the latchkey mechanism 170 will automatically continue to lock the traction exerting mechanism.

From the foregoing description, it will be apparent that the portable traction apparatus 10 of the present invention has a number of advantages, some of which have been described herein, for example it is relatively simple to use, of relatively simple construction, patient controlled, and very patient friendly, and others of which are inherent in the portable traction apparatus 10. Also modifications can be made to the portable traction apparatus described herein without departing from the spirit or scope of the invention as defined in the accompanying claims. Accordingly, the scope of the present invention is only to be limited as necessitated by the accompanying claims.

I claim:

1. A portable traction apparatus comprising:

a table having an upper or head end and a lower or foot end and including a generally rectangular panel adapted to be placed in a horizontal position;

traction exerting mechanism mounted to the table and including an extension linkage assembly fixed to the table and including articulated pivotally interconnected links, an elongate upper end member connected at an inner end to said linkage assembly and having an outer end extending outwardly of said upper or head end of said table, an elongate lower end member having an inner end connected to said linkage assembly and an outer end extending outwardly of said lower or foot end of said table and, first and second lever arms pivotally connected to and forming part of said linkage assembly, each lever arm having an outer end extending outwardly from one side of said table and arm engaging means at the outer end of each lever arm; and said lever arms being movable from and to a nontraction exerting position near said upper or head end of said table where said elongate end members are in a retracted position within the table and a second position toward said lower or foot end of said table where said extension linkage assembly is extended by the movement of said lever arms so as to extend said elongate end members to which body engaging means can be attached for applying traction to a user/patient lying on the table;

said lever arms with said arm engaging means allowing said user/patient to control the amount of traction force applied by the user/patient's forearm or elbow against the arm engaging means intermittently or continuously.

2. The portable traction apparatus of claim 1 including body engaging means for engaging one or more parts of the body and including traction applying means adapted to be connected to one of said end members.

3. The portable traction apparatus of claim 1 wherein each elongate end member has an upwardly extending member at the outer end thereof and a vertically adjustable strut associated with said generally upwardly extending member.

4. The portable traction apparatus of claim 3 wherein the upper end of each vertical strut has a ring or clasp fixed thereto to which a strap of said body engaging means can be releasably fixed.

5. The portable traction apparatus of claim 3 wherein said vertical struts are vertically adjustable through a distance of between approximately 0 and approximately 18 inches.

6. The portable traction apparatus of claim 3 wherein said vertical struts are vertically adjustable through a distance of approximately 12 inches.

7. The portable traction apparatus of claim 3 wherein said vertical struts are vertically adjustable through a distance which will provide an angle of pull or traction of at least up to 30° to the body engaging means.

8. The portable traction apparatus of claim 3 wherein said vertical struts are vertically adjustable through a distance which will provide an angle of pull or traction of between at least 0° to 30° to the body engaging means.

9. The portable traction apparatus of claim 3 wherein each upwardly extending member has locking means for releasably locking said vertical adjustable strut at a desired upwardly extending position thereof.

10. The portable traction apparatus of claim 3 including body engaging means for engaging one or more parts of the body and including traction applying means adapted to be connected to one of said vertically adjustable struts, the vertical adjustment of said vertically adjustable struts enabling the user/patient to apply traction to different regions of the vertebrae of the spine of a user/patient lying on said table.

11. The portable traction apparatus of claim 10 wherein said body engaging means include a cervical strap assembly comprising a neck pillow and a tension strap forming said traction applying means connected intermediate the ends thereof to said pillow and adapted to be releasably and firmly coupled to the vertically adjustable strut extending from said upper elongate end member, and a head strap adapted to be position over the forehead of the user/patient and releasably fixed to said tension strap.

12. The portable traction apparatus of claim 10 wherein said body engaging means include a lumbar strap assembly comprising a halter received about the pelvic area and a tension strap forming said traction applying means fixed to and extending from said halter in the area beneath the hips and having an outer end adapted to be releasably and firmly coupled to said upwardly extending member or to said vertically adjustable strut.

13. The portable traction apparatus of claim 10 wherein said body engaging means include a chest strap assembly comprising a halter which is received about the chest and a strap forming said traction applying means fixed to and extending from said halter at a location beneath the user/patient lying on said table and having an outer adapted to be releasably and firmly coupled to said upwardly extending member or said vertically adjustable strut for holding the user/patient in traction when lumbar traction is applied to the lower spinal region of the user/patient.

14. The portable traction apparatus of claim 1 further including a leg rest assembly mounted to said table for supporting the user/patient's legs in an upper flexed position.

15. The portable traction apparatus of claim 14 wherein said leg rest assembly includes means for adjusting the height of same above said table.

16. The portable traction apparatus of claim 1 wherein each arm engaging means includes an arm pad fixed to and extending upwardly from said outer end of said lever arm.

17. The portable traction apparatus of claim 1 wherein said table includes a pad or mat mounted on an upper surface of said table.

18. The portable traction apparatus of claim 1 wherein said table comprises a top panel, a bottom panel, an upper end wall, a lower end wall and opposed side walls, said upper and lower end walls each having a slot therein through which one of said elongate end members extends and each of said side walls having a slot therein through which one of said lever arms extends.

19. The portable traction apparatus of claim 1 including corner legs at each corner of said table for supporting said table in a horizontal position above a supporting surface.

20. The portable traction apparatus of claim 19 wherein said legs are foldable under the side edges of the table with the lower end of each leg forming a handle for carrying the table when it is situated in a generally vertical position.

21. The portable traction apparatus of claim 1 including latching means for latching the traction exerting mechanism in a desired position for the application of continuous traction simultaneously or separately to the cervical and/or lumbar spinal regions of the user/patient's spine.

22. The portable traction apparatus of claim 21 wherein said latching means include spaced apart detents on one of said elongate end members and a latch bar releasably engageable with one of said detents.

23. The portable traction apparatus of claim 21 wherein said latching means includes an operating member situated on one side of said table and operable by the user/patient to latch or unlatch said latching means.

24. The portable traction apparatus of claim 1 wherein said extension linkage assembly is connected to the underside of said table panel.

25. The portable traction apparatus of claim 1 wherein said extension linkage assembly includes a pivot connection of each lever arm to said table, said lever arms also being pivotally connected to at least one of two links of said linkage assembly, and each said link being pivotally coupled to said inner end of said elongate lower end member.

26. The portable traction apparatus of claim 25 wherein said linkage assembly includes a middle link fixed to said table and extending coaxially with said elongate upper and lower end members, said lever arms being pivotally connected to one end of said middle link at a point inwardly of the inner end of each lever arm, the inner end of each of said lever arms also, being pivotally connected to a connecting link, the other end of which is pivotally connected to a cross-link, each of said cross-links being pivotally connected to the other end of said middle link intermediate the ends of said cross-links with the other end of each cross-link being pivotally connected to one of two links which extends to and is pivotally connected at its other end to said inner end of said elongate lower end member.

27. The portable traction apparatus of claim 25 wherein said lever arms are coupled to another two operating links of said linkage assembly which two operating links are pivotally connected to said inner end of said elongate upper end member.

28. The portable traction apparatus of claim 1 including a vibrating mechanism mounted to said table.

29. A portable traction apparatus comprising: frame means; body support means on said frame means; head extension means movably mounted to said frame means; lower body extension means movably mounted to said frame means; and linkage means in a plane generally coupled between said head extension means and said body extension means and including left and right user engagable movable lever arms which are movable in a plane generally parallel to said support means to increase the distance between the head extension means and the lower body extension means to apply traction to a user/patient lying on the body support means.

30. A portable traction apparatus of claim 29 further comprising head attachment means coupled to said head extension means for attaching the head extension means to a user's head.

31. The portable traction apparatus of claim 29 further comprising lower body attachment means coupled to said lower body extension means for attaching the lower body extension means to a user's lower body.

32. A portable traction apparatus comprising:

base frame means having a longitudinal axis and along said longitudinal axis an upper end and a lower end; head extension means; lower body extension means; linkage means attached to said base frame means and coupled to said head extension means and to said lower body extension means, said linkage means comprising right and left elongate lever arms each having an outer end and an inner end and each lever arm being pivotally attached to said base frame means and being movable in a plane generally parallel to said longitudinal axis; said linkage means being operable to move said head extension means away from the upper end of said base frame means and along the longitudinal axis, and to move said lower body extension means away from the lower end of said base frame means and along the longitudinal axis upon engagement and movement of said lever arms by a user of the apparatus;

body support means attached to said base frame means;

head attachment means attached to said head extension means; and lower body attachment means attached to said lower body extension means.

33. The portable traction apparatus of claim 32 wherein said head extension means comprises an elongate rod having an upper end and a lower end and wherein said upper end is provided with attachment for attaching to said head attachment means and wherein said lower end is coupled to said linkage means.

34. The portable traction apparatus of claim 32 wherein said lower body extension means include an elongate rod having an upper end and a lower end and wherein said upper end is provided with means for attaching to said lower body attachment means and wherein said lower end is coupled to said linkage means.

35. The portable traction apparatus of claim 32 wherein said base frame means includes a substantially rectangular planar surface and, a rim extending from said surface and linkage attachment means mounted on said surface.

36. The portable traction apparatus of claim 35 wherein said rim is provided with said apertures through which the outer ends of each of said lever arms extend.

37. The portable traction apparatus of claim 36 further comprising locking means associated with one of said lever arms for locking said lever arms in place.

38. The portable traction apparatus of claim 35 wherein said rim is provided with an aperture at the upper end through which said head extension means is slidably disposed and an aperture at the lower end through which said lower body extension means is slidably disposed.

39. The portable traction apparatus of claim 32 further comprising leg elevation means.

40. A portable traction apparatus comprising: frame means; body support means on said frame means; lower body extension means movably mounted to said frame means; and linkage means in a plane generally parallel to said body support means coupled to said body extension means and including left and right user engagable movable in a plane lever arms movable generally parallel to said body support means to apply traction to the body of the user by extending the lower body extension means away from said body support means.

41. The portable traction apparatus of claim 27 wherein said lever arms are each coupled directly to said inner end of said elongate lower end member by a single link pivotally connected to said lever arm at one end and pivotally connected to said inner end of said elongate lower end member at the other end.

42. The portable traction apparatus of claim 40 further comprising lower body attachment means coupled to said lower body extension means for attaching the lower body extension means to a user's body.

43. A portable traction apparatus comprising: frame means; body support means on said frame means; head extension means movably mounted to said frame means; and linkage means in a plane generally parallel to said body support means coupled to said head extension means and including left and right user engagable movable in a plane lever arms movable generally parallel to said body support means to apply traction to the head of the user by extending the head extension means away from said body support means.

44. A portable traction apparatus of claim 43 further comprising head attachment means coupled to said head extension means for attaching the head extension means to a user's head.

45. A portable traction apparatus comprising:

base frame means having a longitudinal axis and along said longitudinal axis an upper end and a lower end; lower body extension means; linkage means attached to said base frame means and coupled to said lower body extension means, said linkage means comprising right and left elongate lever arms each having an outer end and an inner end and each lever arm being pivotally attached to said base frame means and being movable in a plane generally parallel to said longitudinal axis;

said linkage means being operable to move said lower body extension means away from the lower end of said base frame means and along the longitudinal axis upon engagement and movement of said lever arms by a user of the apparatus;

body support means attached to said base frame means; and lower body attachment means attached to said lower body extension means.

46. A portable traction apparatus comprising:

base frame means having a longitudinal axis and along said longitudinal axis an upper end and a lower end; head extension means; linkage means attached to said base frame means and coupled to said head extension means, said linkage means comprising right and left elongate lever arms each having an outer end and an inner end and each lever arm being pivotally attached to said base frame means and being movable in a plane generally parallel to said longitudinal axis;

said linkage means being operable to move said head extension means away from the upper end of said base frame means and along the longitudinal axis upon engagement and movement of said lever arms by a user of the apparatus;

body support means attached to said base frame means; and, head attachment means attached to said head extension means.

47. A portable traction apparatus comprising:

a table having an upper or head end and a lower or foot end and including a generally rectangular panel adapted to be placed in a horizontal position;

traction exerting mechanism mounted to the table and including an extension linkage assembly fixed to the table and including articulated pivotally interconnected links, an elongate lower end member having an inner end connected to said linkage assembly and an outer end extending outwardly of said lower or foot end of said table and, first and second lever arms pivotally connected to and forming part of said linkage assembly, each lever arm having an outer end extending outwardly from one side of said table and arm engaging means at the outer end of each lever arm; and said lever arms being movable in a plane generally parallel to said table from and to a nontraction exerting position near said upper or head end of said table where said elongate end members are in a retracted position within the table and a second position toward said lower or foot end of said table where said extension linkage assembly is extended by the movement of said lever arms so as to extend said elongate end members to which body engaging means can be attached for applying traction to a user/patient lying on the table;

said lever arms with said arm engaging means allowing said user/patient to control the amount of traction force applied by the user/patient's forearm or elbow against the arm engaging means intermittently or continuously.

48. The portable traction apparatus of claim 47 including body engaging means for engaging one or more parts of the body and including traction applying means adapted to be connected to said lower end member.

49. The portable traction apparatus of claim 48 wherein said elongate lower end member has an upwardly extending member at the outer end thereof and a vertically adjustable strut associated with said generally upwardly extending member to which said body engaging means is connected.

50. The portable traction apparatus of claim 49 wherein the upper end of each of said vertical strut has a ring or clasp fixed thereto to which a strap of said body engaging means can be releasably fixed.

51. The portable traction apparatus of claim 49 wherein said vertical strut is vertically adjustable through a distance of between approximately 5 and approximately 12 inches.

52. The portable traction apparatus of claim 49 wherein said vertical strut is vertically adjustable through a distance which will provide an angle of pull or traction of between 0° and 45° from the horizontal to the body engaging means.

53. The portable traction apparatus of claim 49 wherein said upwardly extending member has locking means for releasably locking said vertical adjustable strut at a desired upwardly extending position thereof.

54. The portable traction apparatus of claim 49 including body engaging means for engaging one or more parts of the body and including traction applying means adapted to be connected to said vertically adjustable strut, said vertical adjustment of said vertically adjustable strut enabling the user/patient to apply traction to different regions of the vertebrae of the spine of a user/patient lying on said table.

55. The portable traction apparatus of claim 49 wherein said body engaging means include a lumbar strap assembly comprising a halter received about the pelvic area and a tension strap forming said traction applying means fixed to and extending from said halter in the are beneath the hips and having an outer end adapted to be releasably and firmly coupled to said vertically adjustable strut.

56. The portable traction apparatus of claim 47 further including a leg rest assembly mounted to said table for supporting the user/patient's legs in an upper flexed position.

57. The portable traction apparatus of claim 56 wherein said leg rest assembly includes means for adjusting the height of same above said table.

58. The portable traction apparatus of claim 47 wherein said table comprises a top panel, a bottom panel, an upper end wall, a lower end wall and opposed side walls, said upper and lower end walls each having a slot therein through which one of said elongate end members extends and each of said side walls having a slot therein through which one of said lever arms extends.

59. The portable traction apparatus of claim 47 including corner legs at each corner of said table for supporting said table in a horizontal position above a supporting surface.

60. The portable traction apparatus of claim 47 including latching means for latching the traction exerting mechanism in a desired position for the application of continuous traction simultaneously or separately to the cervical and/or lumbar spinal regions of the user/patient's spine.

61. The portable traction apparatus of claim 47 wherein said extension linkage assembly is connected to the underside of said table panel.

62. The portable traction apparatus of claim 47 wherein said extension linkage assembly includes a pivot connection of each lever arm to said table, said lever arms also being pivotally connected to one of two links of said linkage assembly, and each said link being pivotally coupled to said inner end of said elongate lower end member.

63. The portable traction apparatus of claim 47 including a vibrating mechanism mounted to said table.

64. A portable traction apparatus comprising:

a table having an upper or head end and a lower or foot end and including a generally rectangular panel adapted to be placed in a horizontal position;

traction exerting mechanism mounted to the table and including an extension linkage assembly fixed to the table and including articulated pivotally interconnected links, an elongate upper end member connected at an inner end to said linkage assembly and having an outer end extending outwardly of said upper or head end of said table, and first and second lever arms pivotally connected to and forming part of said linkage assembly, each lever arm having an outer end extending outwardly from one side of said table and arm engaging means at the outer end of each lever arm; and said lever arms being movable in a plane generally parallel to said table from and to a nontraction exerting position near said upper or head end of said table where said upper elongate end member is in a retracted position within the table and a second position toward said lower or foot end of said table where said extension linkage assembly is extended by the movement of said lever arms so as to extend said elongate lower end member to which body engaging means can be attached for applying traction to a user/patient lying on the table;

said lever arms with said arm engaging means allowing said user/patient to control the amount of traction force applied by the user/patient's forearm or elbow against the arm engaging means intermittently or continuously.

65. The portable traction apparatus of claim 64 including body engaging means for engaging one or more parts of the body and including traction applying means adapted to be connected to said upper end member.

66. The portable traction apparatus of claim 64 wherein said elongate upper end member has an upwardly extending member at the outer end thereof and a vertically adjustable strut associated with said generally upwardly extending member.

67. The portable traction apparatus of claim 66 wherein the upper end of said vertical strut has a ring or clasp fixed thereto to which a strap of said body engaging means can be releasably fixed.

68. The portable traction apparatus of claim 67 wherein said vertical strut is vertically adjustable through a distance of between approximately 5 and approximately 12 inches.

69. The portable traction apparatus of claim 67 wherein said vertical strut is vertically adjustable through a distance which will provide an angle of pull or traction of between 0° and 45° from the horizontal to the body engaging means.

70. The portable traction apparatus of claim 67 wherein said upwardly extending member has locking means for releasably locking said vertical adjustable strut at a desired upwardly extending position thereof.

71. The portable traction apparatus of claim 67 including body engaging means for engaging one or more parts of the body and including traction applying means adapted to be connected to said vertically adjustable strut, said vertical adjustment of said vertically adjustable strut enabling the user/patient to apply traction to different regions of the vertebrae of the spine of a user/patient lying said said table.

72. The portable traction apparatus of claim 67 wherein said body engaging means include a cervical strap assembly comprising a neck pillow and a tension strap forming said traction applying means connected intermediate the ends thereof to said pillow a d adapted to be releasably and firmly coupled to the vertically adjustable strut extending from said upper elongate end member, and a head strap adapted to be position over the forehead of the user/patient and releasably fixed to said tension strap.

73. The portable traction apparatus of claim 64 including latching means for latching the traction exerting mechanism in a desired position for the application of continuous traction simultaneously or separately to the cervical and/or lumbar spinal regions of the user/patient's spine.

74. The portable traction apparatus of claim 64 wherein said extension linkage assembly includes a pivot connection of each lever arm to said table, said lever arms also being pivotally connected to one of two links of said linkage assembly, and each said link being pivotally coupled to said inner end of said elongate lower end member.

75. The portable traction apparatus of claim 64 including a vibrating mechanism mounted to said table.

76. The portable traction apparatus of claim 64 including corner legs at each corner of said table for supporting said table in a horizontal position above a supporting surface.

* * * * *

UNITED STATES PATENT AND TRADEMARK OFFICE

CERTIFICATE OF CORRECTION

PATENT NO. : 5,052,378

DATED : October 1, 1991

INVENTOR(S) : Ralph M. Chitwood et al

It is certified that error appears in the above-indentified patent and that said Letters Patent is hereby corrected as shown below:

On the title page:

Abstract, Line 3 "foot and" should be --foot end and--.

Abstract, line 11 "table and or," should be --table and/or,--.

Column 4, line 3 "thereby" should be --whereby--.

Column 5, line 24 "viewing latching" should be--viewing the latching--.

Column 6, line 32 "wall !4" should be --wall 14--.

Column 7, line 18 "transversely &through" should be --transversely through--.

Column 9, line 59 "Velcro TM" should be --hook and loop material such as that sold under the trademark VELCRO--.

Column 12, line 15 "may" should be --many--.

Column 12, line 26 "apparats" should be --apparatus--.

Column 14, line 57 "outer adapted" should be --outer end adapted--.

UNITED STATES PATENT AND TRADEMARK OFFICE
CERTIFICATE OF CORRECTION

PATENT NO. : 5,052,378
DATED : October 1, 1991
INVENTOR(S) : Ralph M. Chitwood et al It is certified that error appears in the above-indentified patent and that said Letters Patent is hereby corrected as shown below:

Column 16, lines 11-11 "generally coupled" should be --generally parallel to said body support means coupled--.

Column 16, line 13 "said support" should be --said body support--.

Column 17, line 22 & lines 42-3 "movable in a plane lever arms movable generally" should be --movable lever arms movable in a plane generally--.

Column 20, line 65 "lying said said table" should be --lying on said table--.

Column 21, line 2 "a d" should be --and--.

Signed and Sealed this

Twenty-fifth Day of October, 1994

Attest:

BRUCE LEHMAN

Attesting Officer

*Commissioner of Patents and Trademarks*